United States Patent
Song et al.

(10) Patent No.: US 11,796,526 B2
(45) Date of Patent: Oct. 24, 2023

(54) DEVICE AND METHOD OF GAS HYDRATE PRESSURE MAINTAINING REPLACEMENT FOR IN-SITU RAMAN ANALYSIS

(71) Applicant: DALIAN UNIVERSITY OF TECHNOLOGY, Liaoning (CN)

(72) Inventors: Yongchen Song, Liaoning (CN); Jiafei Zhao, Liaoning (CN); Man Li, Liaoning (CN); Lei Yang, Liaoning (CN); Weiguo Liu, Liaoning (CN); Mingjun Yang, Liaoning (CN); Yanghui Li, Liaoning (CN); Zheng Ling, Liaoning (CN); Yu Liu, Liaoning (CN); Yi Zhang, Liaoning (CN); Dayong Wang, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 748 days.

(21) Appl. No.: 16/968,491

(22) PCT Filed: Aug. 31, 2019

(86) PCT No.: PCT/CN2019/103887
§ 371 (c)(1),
(2) Date: Aug. 7, 2020

(87) PCT Pub. No.: WO2021/035753
PCT Pub. Date: Mar. 4, 2021

(65) Prior Publication Data
US 2021/0072216 A1    Mar. 11, 2021

(51) Int. Cl.
*G01N 33/22* (2006.01)
*G01N 21/01* (2006.01)
(Continued)

(52) U.S. Cl.
CPC ............. *G01N 33/225* (2013.01); *G01N 1/42* (2013.01); *G01N 21/01* (2013.01); *G01N 21/65* (2013.01)

(58) Field of Classification Search
CPC ........ G01N 33/225; G01N 1/42; G01N 21/01; G01N 21/65
See application file for complete search history.

(56) References Cited

FOREIGN PATENT DOCUMENTS

| CN | 1762565 A | 4/2006 |
|---|---|---|
| CN | 101451985 A | 6/2009 |

(Continued)

OTHER PUBLICATIONS

Espacenet English Machine Translation of WO 2017/107639. (Year: 2017).*

*Primary Examiner* — Jennifer Wecker
*Assistant Examiner* — Kathryn Elizabeth Limbaugh
(74) *Attorney, Agent, or Firm* — MUNCY, GEISSLER, OLDS & LOWE, P.C.

(57) ABSTRACT

The invention discloses a gas hydrate pressure maintaining replacement device and method for in-situ Raman analysis. Comprehensive experiments such as the formation/decomposition/displacement of high-pressure gas hydrates can be realized, and in-situ Raman characterization can be performed. Including reaction kettle system with temperature control unit, pressure control gas supply system, pressure holding system, replacement gas system, sample pre-cooling system, vacuum system and data acquisition and processing system. The device can solve the problem that the Raman peak position of the 512 cage is covered by the Raman peak position of the gas when the high-pressure gas hydrate is characterized in situ in the reaction kettle, at the same time, (Continued)

Figure 1:
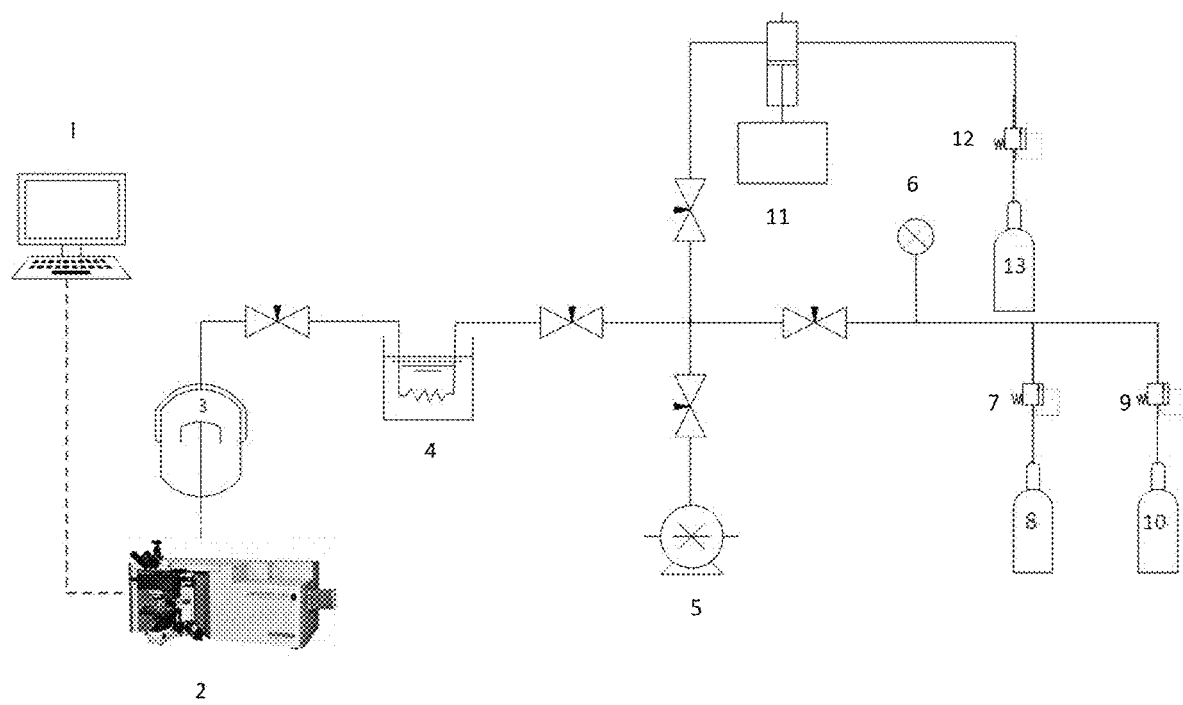

it solves the problems of sampling difficulties in ex-situ Raman characterization and experimental errors caused by sample transfer.

3 Claims, 2 Drawing Sheets

(51) Int. Cl.
  *G01N 1/42* (2006.01)
  *G01N 21/65* (2006.01)

(56) References Cited

FOREIGN PATENT DOCUMENTS

| | | | |
|---|---|---|---|
| CN | 103278374 | A | 9/2013 |
| CN | 106000229 | A | 10/2016 |
| CN | 106680239 | A | 5/2017 |
| CN | 108758330 | A | 11/2018 |
| KR | 20120023912 | A | 3/2012 |
| WO | WO-2017107639 | A1 * | 6/2017 |

* cited by examiner

DEVICE AND METHOD OF GAS HYDRATE PRESSURE MAINTAINING REPLACEMENT FOR IN-SITU RAMAN ANALYSIS

TECHNICAL FIELD

The invention belongs to the field of hydrate dynamics, and relates to a device of gas hydrate pressure maintaining and replacing used for in-situ Raman characterization. In particular, it relates to a kind of experimental study suitable for in-situ observation of gas hydrate pressure-replacement kinetics.

BACKGROUND

The demand of world natural gas market increased by 96 billion cubic meters in 2017, up 3% year-on-year in 2016, which is the fastest growth rate since 2010. The huge demand for natural gas has prompted the rapid development of natural gas hydrate and shale gas resources. Among them, natural gas hydrates were officially listed as minerals in 2017 due to their huge reserves of 80 billion tons of oil equivalent (China) and were tested in the Shenhu area of the South China Sea. The mining methods of natural gas hydrate mainly include: depressurization method, thermal stimulation method, inhibitor method and $CO_2$ replacement method. Among them, the $CO_2$ replacement method is regarded as the most promising mining method in the future because it can store $CO_2$ for a long period while solving natural gas and solve geological problems such as submarine landslides caused by natural gas hydrate mining. However, due to the complex reaction kinetics during the $CO_2$ replacement process, the reaction mechanism is not yet clear, it is extremely important to study the micro-mechanism of the experiment process of $CO_2$ replacement of natural gas hydrate. However, the current experimental equipment is basically based on macro experiments or ex-situ Raman experimental design, that is, the sample is transferred to a high-pressure capillary for Raman spectroscopy measurement after the hydrate sample is generated, or the gas phase $CH_4$ in the reactor is discharged before $CO_2$ is introduced. But the replacement method of exhaust gas is a high probability to cause the decomposition of the initial hydrate sample during microscopic characterization, which makes the replacement experiment efficiency higher. Therefore, it is very necessary to design a hydrate high-pressure holding experimental device suitable for in-situ Raman spectroscopy. When mining natural gas hydrate deposits, the hydrate reservoir still contains high-pressure natural gas hydrate, so the pressure replacement experiment is more in line with the actual mining process. At present, there are few pressure-maintaining replacement experimental pipelines for micro-equipment such as Raman spectrometer, PXRD, neutron diffraction and so on, and it is difficult to satisfy the current research on the dynamic mechanism of $CO_2$ replacement mining natural gas hydrate, so that, in terms of measurement accuracy and mining practicability, a high-pressure holding device suitable for in-situ Raman spectroscopy is very necessary.

The Raman spectrometer performs time-resolved in-situ non-destructive measurement of the dynamic mechanism of $CO_2$ replacement gas hydrate production, which is a reliable method for measuring micro-areas, so it is widely used to characterize the kinetics of hydrate replacement at the molecular level. However, in the in-situ Raman analysis of gas hydrate displacement experiments, the peak of C—H symmetric stretching which belongs to the gas will cover the peak of gas hydrate, which means the $5^{12}$ cage C—H symmetric stretching vibration, leading to the difficulties to recognize the filling of the gas hydrate $5^{12}$ cage. Moreover, this problem cannot be solved through the optimization of instrument parameters, which brings difficulties to the dynamic analysis of guest molecular filling. Therefore, this patent proposes a high-pressure holding pressure experiment device suitable for in-situ Raman spectroscopy measurement. The gas hydrate in-situ position change and quantitative characterization can be performed on the device, and the device is simple and easy to operate, which is suitable for all open Raman spectrometry.

At present, laboratories mostly perform ex-situ Raman characterization of hydrate growth because the limitation of the experimental conditions. Ex-situ characterization is that the hydrate sample is quickly transferred to a closed container in a cold storage for Raman spectroscopy characterization after the hydrate sample is generated, the disadvantage of this method is that for samples that require high-pressure and low-temperature conditions such as $CH_4$ and $CO_2$ hydrates, the lack of reaction gas maintenance and low-temperature conditions during the transfer and characterization will lead to rapid decomposition of the hydrate surface layer and lower temperatures. It also adsorbs water vapor in the air to form ice on the surface of the hydrate sample, which results in a low hydrate occupancy and reduced reliability. This error may be negligible for qualitative analysis, but for quantitative analysis it is an important reason for the unreliability of experimental results. The few devices suitable for in-situ Raman characterization of hydrates, such as the CN103278374B patent, propose an in-situ Raman analysis and hydrate characterization device and an in-situ Raman analysis method for hydrate samples, it is only suitable for vertical horizontal optical path Raman spectrometer measurement, and it is completely unsuitable for the wider vertical optical path Raman spectrometer. The experimental device also has the disadvantages of complicated experimental device and large experimental error.

With the development of instrument science and the in-depth study of hydrate kinetics, there is an urgent need for a comprehensive high-pressure pressure-holding hydrate comprehensive experimental system suitable for in-situ Raman characterization to meet the microscopic characterization of the hydrate structure and improve the accuracy of the experiment.

SUMMARY OF THE INVENTION

In view of the shortcomings of the prior art, the present invention provides an experimental device suitable for in-situ Raman characterization of high-pressure holding pressure hydrate replacement characterization. Comprehensive experiments such as replacement characterization of high-pressure gas hydrates can be realized, not only the in-situ qualitative analysis of the hydrate dynamic process can be realized, but also the determination of the gas peak of $5^{12}$ cage in the hydrate by the C—H bond stretching vibration is excluded, which can be used for quantitative characterization of hydrates.

The invention provides a gas hydrate pressure-maintaining replacement device for in-situ Raman analysis, includes a Raman spectrometer, a reaction kettle system, a sample pre-cooling system, a pressure-controlled gas supply system, a vacuum system, and a data acquisition and processing system, the reaction kettle system is placed on the XY operating table of the Raman spectrometer.

The reaction kettle system includes a visualization hydrate reaction kettle, a temperature sensor and a liquid nitrogen temperature control component; The top surface of the reaction kettle is provided with a sapphire window, of which the Raman peak position is sharp and easy to separate from the gas hydrate signal, so the error caused by the window material can be avoided. Liquid nitrogen inlet/outlet is provided on the side for temperature control, the temperature range is −196° C.-600° C., and the pressure range is −0.1 MPa-10 MPa; The temperature sensor is set on the sample table in the reactor, and the protective sleeve outside the reactor is equipped with a liquid nitrogen purge device for external temperature circulation and the weaked signal caused by frosting of the window. The casing is equipped with a liquid nitrogen purge pipe to maintain the overall low temperature of the reactor and prevent frosting of the visible window impede measurement.

The pressure-controlled gas supply system includes a pressure regulating valve A and a replaced gas cylinder connected by a pipeline; The pressure regulating valve A is used to switch the pipeline and adjust the pipeline pressure according to the target pressure to provide stable replaced gas to generate initial hydrate.

The pressure maintaining system includes a pressure regulating valve B and an isotope gas cylinder connected through a pipeline. The pressure regulating valve B is used to adjust the pressure of the circuit, and the isotope gas is used to maintain the pressure after the displaced gas is discharged. Due to the coincidence of the gas hydrate gas phase peak and the $5^{12}$ cage peak in the hydrate phase, the filling of the hydrate $5^{12}$ cage cannot be analyzed. However, the difference between the Raman peak position of the isotope gas and the ordinary gas is about 800 cm', and because it is an allotrope, and the physical properties are similar, so using isotopic gas to maintain the confining pressure of the gas hydrate can solve the single gas hydration problems in the in-situ experiment of objects.

The sample pre-cooling system includes a water bath and an attached temperature control unit; The inlet of the sample pre-cooling system is connected to the parallel pressure-holding system and the pressure-controlled gas supply system to pre-cool the gas provided in the pressure-controlled gas supply system or pressure-maintaining system to prevent hydrates decomposition caused by the gas during gas injection. The outlet of the sample pre-cooling system is connected to the reactor system, and the gas after pre-cooling is sent to the reactor.

The replacement gas system includes a plunger pump, an anti-corrosion pressure regulating valve and a replacement gas cylinder connected in sequence through the pipeline, and the cylinder is mainly CO2 or mixed gas cylinders; The plunger pump is used to store gas and accurately adjust the pressure in the replacement pipeline, and the anti-corrosion pressure regulating valve and replacement gas cylinder are used to provide replacement gas.

The vacuum system includes a vacuum pump connected to the pipeline by a T-shaped pipe interface. The vacuum pump is used to evacuate the visualization hydrate reactor before the reaction, to eliminate the influence of impurity gas in the reactor on the Raman analysis, and to quickly exhaust the gas after the reaction.

The data acquisition and processing system is used to collect the temperature of the temperature sensor and the various data of the Raman spectrum of the sample for analysis. It can perform visual observation with a maximum magnification of 100 times and Raman spectrum measurement and analysis with an accuracy of $0.1$ cm$^{-1}$.

The method for adopting the above-mentioned gas hydrate pressure-replacement device for in-situ Raman analysis includes the following steps:

Step 1: Firstly deionized water is added to the reaction kettle, and the temperature sensor and liquid nitrogen temperature control component are used to reduce the temperature of the reaction kettle to below 0° C. to freeze the deionized water, which can prevent water from being drawn out of the reaction kettle due to vacuum. Secondly the vacuum pump and valve is turned on after the sample freezing, and the vacuum pump and valve are closed after evacuating the reactor;

Step 2: Firstly, the needle valve is closed that is located at the connection between the sample pre-cooling device and the reactor. Secondly, the knob of the replaced gas cylinder is unscrewed that located in the pressure-controlled gas supply system, and the pressure regulating valve A is adjusted to make the gas pressure in the pipeline to the target pressure, and let it stand until the digital pressure gauge shows that the pressure is stable. At this time, the replaced gas is pre-cooled to the target temperature. Thirdly, the needle valve of the sample pre-cooling device is opened to send the pre-cooled replaced gas into the reaction kettle, meanwhile, the reaction temperature is adjusted to the target temperature, you can see that the hydrate quickly forms when the target temperature is approached;

Step 3: Determine the hydrate formation by Raman spectroscopy. When the formation of methane hydrate is complete, that is, the cage occupancy rate is more than 90%, the temperature of the reaction kettle is reduced to below −80° C. through the liquid nitrogen temperature control component. The experimental results show that the hydrate decomposition is extremely slow at −80° C., and the hydrate decomposition is less than 0.1% during the replacement for 1 hour. Firstly, the vacuum pump is turned on to draw vacuum after the temperature is stable, and then the vacuum pump and the needle valve of the pressure-controlled gas supply system and the pre-cooling system are closing after vacuuming. Secondly the needle valve of the pressure holding system is opened and the knob of the isotope gas cylinder is unscrewed, then the pressure in the gas pipeline is adjusted to the target pressure. The isotope gas in the pre-cooling system is pre-cooled to prevent the decomposition by the heat of gas during gas injection. Thirdly the needle valve of the pre-cooling system is opened to pass the pre-cooled isotope gas into the reactor to maintain the pressure;

Step 4: Firstly, the pressure regulating valve B of the pressure holding system is closed and the replacement gas cylinder of the replacement gas system is opened. Secondly, the anti-corrosion pressure regulating valve is adjusted to the required pressure, and the plunger pump valve is opened. So that the replacement gas could be pre-cooled through the sample pre-cooling system to prevent the gas from decomposition by carrying heat of gas;

Step 5: The needle valve of the pre-cooling system is opened to pass the pre-cooled replacement gas into the reactor, after the ventilation is completed, the temperature is raised to the replacement temperature, and the pressure is adjusted to maintain the pressure in the reactor at the target pressure; and Step 6: In steps 1 to 5, the temperature parameters in the reactor are collected by temperature sensors, and the spectral data is collected by Raman spectrometer at regular intervals to monitor the hydrate formation and filling rate changes in the reactor in real time.

The beneficial effects of the present invention are: The device is suitable for in-situ generation and Raman characterization of high-pressure gas hydrates. There are three advantages for that: 1) The experimental error is eliminated caused by the transfer of test samples in non-in-situ experiments. 2) The problem is solved that some peak positions cannot be quantified due to peak position overlap in in-situ experiments. 3) It's suitable for long-scale gas hydrate in-situ position exchange studies. It is a necessary device for exploring the microscopic mechanism of displacement reaction and is applicable to all open Raman spectrometers.

BRIEF DESCRIPTION

FIG. 1: a schematic diagram of an experimental apparatus of the present invention suitable for in-situ Raman characterization of gas hydrate replacement.

In the figure: 1 Computer; 2 Raman spectrometer; 3 Visualized hydrate reactor; 4 Pre-cooled spiral pipe; 5 Vacuum pump; 6 Digital display pressure gauge; 7 pressure regulating valve A; 8 replaced gas cylinder; 9 pressure regulating valve B; 10 Isotope gas cylinder; 11 plunger pump; 12 Anti-corrosion pressure regulating valve C; 13 Replacement gas cylinder.

Figure 2:
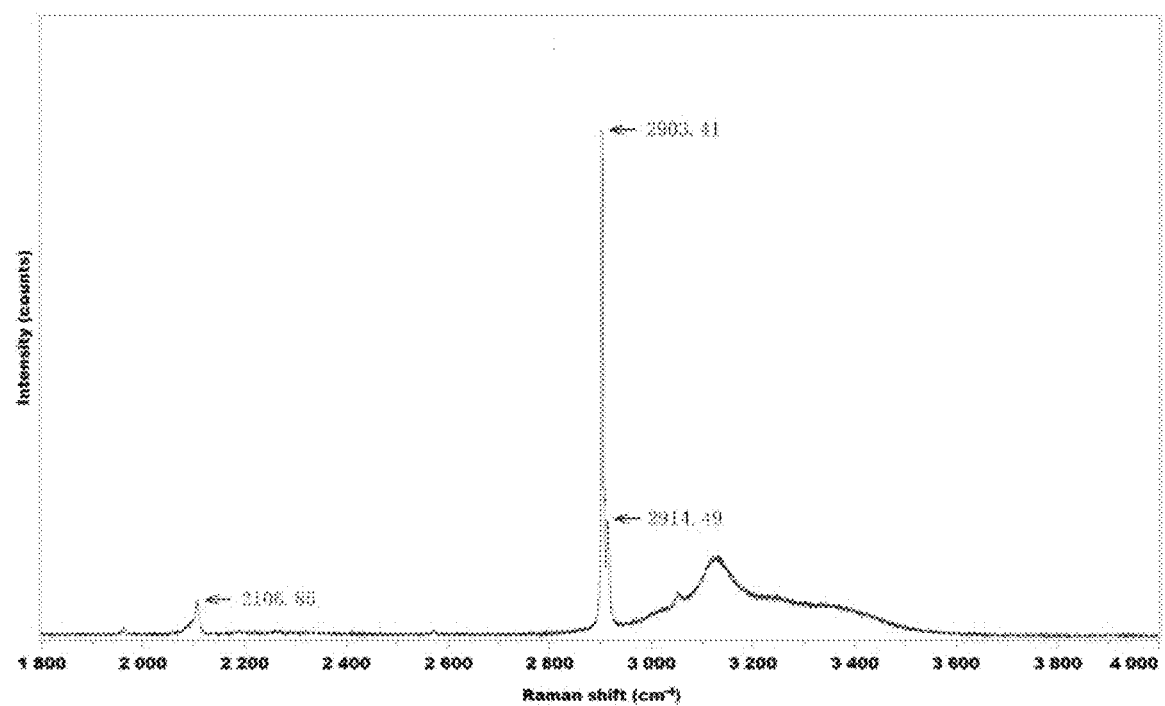

FIG. 2: the in-situ Raman experimental data of deuterated methane gas to maintain methane hydrate.

DETAILED DESCRIPTION

Example 1

This embodiment is an experimental device suitable for in-situ Raman characterization of $CO_2$ displacement high-pressure methane hydrate formation/decomposition/displacement by pressure-holding method. Taking the experiment of replacing methane hydrate with $CO_2$ as an example, referring to FIG. 1, the experimental process is as follows:

The replaced gas cylinder 8 is filled with high-purity methane gas with a purity of 99.99%, the isotope gas cylinder 10 is filled with scientific grade full deuterium methane gas with a purity of 99.98%, and the replacement gas cylinder 13 is filled with 98.99% purity gas;

Step 1: Firstly, deionized water is added to the reactor 3. Secondly, the temperature sensor and liquid nitrogen temperature control components are used to reduce the temperature of the reactor 3 to below 0° C. to freeze the deionized water and prevent the water from being drawn out of the reactor 3 due to vacuum. Thirdly, the vacuum pump 5 and the valve are turned on, so that the reaction kettle 3 is evacuated and the vacuum pump 5 and the valve is closed after the sample freezing;

Step 2: Firstly, the needle valve is closed which is located at the connection between the sample pre-cooling device 4 and the reaction kettle 3. Secondly, the knob of the methane gas cylinder is unscrewed which located in the pressure-controlled gas supply system and the pressure regulating valve A 7 is adjusted to make the gas pressure in the pipeline the target pressure, and let it stand until the digital pressure gauge 6 shows that the pressure is stable. Now the temperature is adjusted to the target temperature. Thirdly, the needle valve of the sample pre-cooling device 4 is opened to send the pre-cooled methane body to the reaction kettle 3, and at the same time the reaction temperature is raised to the target temperature, you can see that the hydrate quickly forms when it approaches the target temperature;

Step 3: Determine the hydrate formation by Raman spectroscopy 2. When the formation of methane hydrate is complete, that is, the cage occupancy rate is more than 90%, the temperature of the reaction kettle 3 is reduced to below −80° C. through the liquid nitrogen temperature control component. The experimental results show that the hydrate decomposition is extremely slow at −80° C., and the hydrate decomposition is less than 0.1% during the replacement for 1 hour. Firstly, the vacuum pump 5 is turned on for vacuuming after the temperature is stable, and the vacuum pump 5 and the needle valves, the pressure-controlled gas supply system and the pre-cooling system 4, are turned off after vacuuming. Secondly, the needle valve of the pressure holding system is opened and the knob of the fully deuterated methane gas cylinder 10 is unscrewed, and the pressure in the gas pipeline is adjusted to the target pressure, so that the fully deuterated methane body is pre-cooled in the pre-cooling system to prevent gas from the decomposes by the heat of gas. Thirdly, the needle valve of the pre-cooling system 4 is opened to pass the pre-cooled fully deuterated methane gas into the reactor 3 to maintain the pressure;

Step 4: The gas valve of the pressure-holding system is closed, and the carbon dioxide gas cylinder 13 of the carbon dioxide gas system is opened. The anti-corrosion pressure regulating valve is adjusted to the required pressure. Secondly, the valve of the plunger pump 11 is opened, so that the carbon dioxide gas is pre-cooled through the sample pre-cooling system 4 to prevent the gas from decomposition by the carrying heat of gas;

Step 5: The needle valve of the pre-cooling system 4 is opened to allow the pre-cooled carbon dioxide gas to pass into the reactor 3, and after the ventilation is completed, the temperature is raised to the replacement temperature, and the pressure is adjusted to maintain the pressure in the reactor 3 at the target pressure; and Step 6: In steps 1 to 5, the temperature parameters in the reactor 3 are collected by temperature sensors. The spectral data is collected by Raman spectrometer 2 at regular intervals to monitor the hydrate formation and filling rate changes in the reactor 3 in real time.

Deuterated methane gas maintains the in-situ Raman experimental data of methane hydrate, as shown in FIG. 2. The figure shows the Raman spectrum after maintaining the partial pressure of methane hydrate with deuterated methane for 1 h. Among them, the C—H symmetric stretching vibration peak of methane hydrate is 2904 cm$^{-1}$, and the gas phase peak of deuterated methane is 2103 cm$^{-1}$. The experimental results show that deuterated methane can maintain methane hydrate without decomposition.

Example 2

Taking the experiment of replacing ethane hydrate with $CO_2$ as an example, referring to FIG. 1, the experimental process is as follows:

The replaced gas cylinder 8 is filled with high-purity ethane gas with a purity of 99.99%, the isotope gas cylinder 10 is filled with scientific grade all-deuterium ethane gas with a purity of 99.98%, and the replacement gas cylinder 13 is filled with a purity of 98.99% $CO_2$ gas;

Experimental steps 1-6 are the same as in Example 1. Raman peak of C—H of ethane is between 2850-2950 cm$^{-1}$, Raman peak of C-D of deuterated ethane is between 2050-2150 cm$^{-1}$, similar to methane. Deuterated ethane can maintain the partial pressure of ethane, so in-situ Raman spectroscopy can be performed.

Example 3

This embodiment is a $CO_2$ displacement gas hydrate generation displacement experiment device suitable for in-situ Raman characterization by pressure-holding method. Taking the experiment of $CO_2$ replacement of natural gas hydrate as an example, combined with FIG. 1, the experimental process is as follows:

The gas cylinder 8 to be replaced is a mixture of 95% methane and 5% ethane or propane in any ratio. A proportion of mixed gas, the replacement gas cylinder 13 is filled with $CO_2$ gas with a purity of 98.99%;

Experimental steps 1-6 are the same as in Example 1. The Raman peak of C—H of natural gas is between 2850-2950 cm$^{-1}$, and the Raman peak of C-D of deuterated gas is between 2050-2150 cm$^{-1}$.

Although the patent technology is described above with reference to the drawings, the patent technology is not limited to the above-mentioned embodiment and the above-mentioned experimental gas. The above usage is only for illustration, not for limitation. Under the inspiration of the present invention, the modifications made without departing from the present invention all fall within the protection of the present invention.

The invention claimed is:

1. A gas hydrate pressure-maintaining replacement device for in-situ Raman analysis, wherein the device includes a Raman spectrometer, a reaction kettle system, a sample pre-cooling system, a pressure-controlled gas supply system, a pressure-maintaining system, a vacuum system and a data acquisition and processing system; wherein a reactor system is placed on a XY operating table of the Raman spectrometer;

the reaction kettle system includes a visual hydrate reaction kettle, a temperature sensor, and a liquid nitrogen temperature control component; a window is provided on the top surface of the visual hydrate reaction kettle, and a liquid nitrogen inlet/outlet is provided on the side of the visual hydrate reaction kettle for temperature control; the temperature sensor is set on a sample table in the visual hydrate reaction kettle, the visual hydrate reaction kettle is covered with a plastic insulation shell; a casing is equipped with a liquid nitrogen purge pipe to maintain an overall low temperature state of the visual hydrate reaction kettle and prevent frosting in the window from hindering measurement;

the pressure-controlled gas supply system includes a pressure regulating valve A and a replaced gas cylinder connected by a pipeline to provide stable replaced gas to generate initial hydrate;

the pressure-maintaining system includes a pressure regulating valve B and an isotope gas cylinder connected through a pipeline, the pressure regulating valve B is used to adjust the pressure of the pipeline, and isotope gas is used to maintain the pressure after exhausting the displaced gas;

the sample pre-cooling system includes a water bath and an attached temperature control unit; an entrance of the sample pre-cooling system is connected to the pressure-maintaining system and the pressure-controlled gas supply system, wherein the pressure-maintaining system and the pressure-controlled gas supply system are parallel, which is to pre-cool gas provided in the pressure-control gas supply system or the pressure-maintaining system; an outlet of the sample pre-cooling system is connected to the reactor system, and sends the gas after pre-cooling to a reactor;

a displacement gas system includes a plunger pump, an anti-corrosion pressure regulating valve and a $CO_2$ gas cylinder connected in sequence by a pipeline; the plunger pump is used to accurately adjust the pressure in a $CO_2$ pipeline, and the anti-corrosion pressure regulating valve and $CO_2$ gas cylinder are used to provide a replacement gas $CO_2$;

the vacuum system includes a vacuum pump connected to a pipeline by a pipe joint, which is used to evacuate the visual hydrate reaction kettle before a reaction, to eliminate the influence of impurity gases in the visual hydrate reaction kettle, and to quickly exhaust after the reaction;

the data acquisition and processing system is used to collect the temperature from the temperature sensor and the data of the Raman spectrum of the sample for analysis.

2. A method for using the gas hydrate pressure-maintaining replacement device for in-situ Raman analysis of claim 1, wherein the method includes the following steps:

Step 1: deionized water is added to the visual hydrate reaction kettle, and the temperature sensor and liquid nitrogen temperature control component are used to reduce the temperature of the visual hydrate reaction kettle to below 0° C. to freeze the deionized water; a vacuum pump and valve is turned on after the temperature is stable, and the vacuum pump and valve are closed after evacuating the reactor;

Step 2: a needle valve is closed that is located at a connection between the sample pre-cooling system and the reactor; a knob of the replaced gas cylinder is unscrewed that is located in the pressure-controlled gas supply system, and the pressure regulating valve A adjusts the gas pressure in the pipeline to a target pressure, and let it stand until a digital pressure gauge shows that the pressure is stable; at this time, the pre-cooling of the replaced gas is completed; the needle valve of a precooling device is opened to send the replaced gas into the visual hydrate reaction kettle, at the same time a reaction temperature is raising to a desired temperature;

Step 3: determine a hydrate formation by Raman spectroscopy; when the formation of methane hydrate is complete, that is, the cage occupancy rate is more than 90%, the temperature of the visual hydrate reaction kettle is reduced to below −80° C. through the liquid nitrogen temperature control component; the vacuum pump is turned on to draw vacuum after the temperature is stable, and then the vacuum pump and a needle valve of the pressure-controlled gas supply system and the sample pre-cooling system are closing after vacuuming; a needle valve of the pressure-maintaining system is opened and a knob of the isotope gas cylinder is unscrewed, then the pressure in a gas pipeline is adjusted to the target pressure; the isotope gas in the sample pre-cooling system is pre-cooled; the needle valve of the sample pre-cooling system is opened to pass the pre-cooled isotope gas into the reactor to maintain the pressure;

Step 4: a gas end valve of a pressure holding system is closed and the $CO_2$ gas cylinder of a replacement gas system is opened; the anti-corrosion pressure regulating valve is adjusted to the required pressure, and a plunger pump valve is opened; so that $CO_2$ gas could be pre-cooled through the sample pre-cooling system;

Step 5: the needle valve of the sample pre-cooling system is opened to pass the pre-cooled $CO_2$ gas into the reactor, after the ventilation is completed, the temperature is raised to a replacement temperature;

Step 6: in steps 1 to 5, the temperature parameters in the reactor are collected by the temperature sensor, and spectral data is collected by Raman spectroscopy at regular intervals to monitor the hydrate formation and filling rate changes in the reactor in real time.

3. The method according to claim 2, wherein the replaced gas is one or a mixture of two or more of methane, ethane, and propane.

* * * * *